United States Patent [19]

Scheler

[11] 4,334,004
[45] Jun. 8, 1982

[54] LIGHT-SENSITIVE DIAZOTYPE MATERIAL WITH 2-HYDROXY-3-NAPHTHOIC ACID AMIDES HAVING 6-SULFONIC ACID AMIDE SUBSTITUTION

[75] Inventor: Siegfried Scheler, Wiesbaden, Fed. Rep. of Germany

[73] Assignee: Hoechst Aktiengesellschaft, Fed. Rep. of Germany

[21] Appl. No.: 21,104

[22] Filed: Mar. 16, 1979

[30] Foreign Application Priority Data

Mar. 18, 1978 [DE] Fed. Rep. of Germany ....... 2811981

[51] Int. Cl.³ .......................... G03C 1/58; G03C 1/54
[52] U.S. Cl. ......................................... 430/176; 430/8; 430/172; 430/173; 430/174; 430/150; 430/171; 430/180; 430/183; 544/159; 544/58.1; 260/239 BF; 546/206; 546/86; 548/542
[58] Field of Search ............................ 96/75, 91 R, 49; 430/180, 176, 173, 174, 150, 171, 183, 8

[56] References Cited

U.S. PATENT DOCUMENTS

| | | | |
|---|---|---|---|
| 2,233,038 | 2/1941 | Sus et al. | 96/91 R |
| 2,278,444 | 10/1942 | Weissberger et al. | 96/91 R |
| 2,537,098 | 1/1951 | Slifkin et al. | 96/91 R |
| 2,970,909 | 2/1961 | Slimowicz | 96/91 R |
| 3,113,025 | 12/1963 | Bialczak | 96/91 R |
| 3,272,627 | 9/1966 | Sus et al. | 96/91 R |
| 3,367,776 | 2/1968 | Bialczak et al. | 96/91 R |
| 3,406,071 | 10/1968 | Sus et al. | 96/91 R |

OTHER PUBLICATIONS

Kosar, J., "Light-Sensitive Systems", J. Wiley & Sons, 1965, pp. 220, and 234–239.

*Primary Examiner*—Charles L. Bowers, Jr.
*Attorney, Agent, or Firm*—James E. Bryan

[57] ABSTRACT

This invention relates to 2-hydroxy-3-naphthoic acid amides of the general formula:

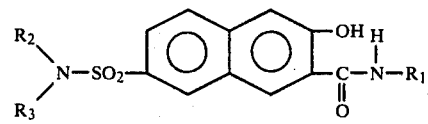

wherein $R_1$ is hydrogen, a substituted or unsubstituted alkyl, cycloalkyl, aralkyl, or aryl group, and $R_2$ and $R_3$ are identical or different and are hydrogen, a substituted or unsubstituted alkyl, cycloalkyl, aralkyl, or aryl group, or, together with the nitrogen atom to which they are attached, a substituted or unsubstituted heterocyclic group.

10 Claims, 2 Drawing Figures

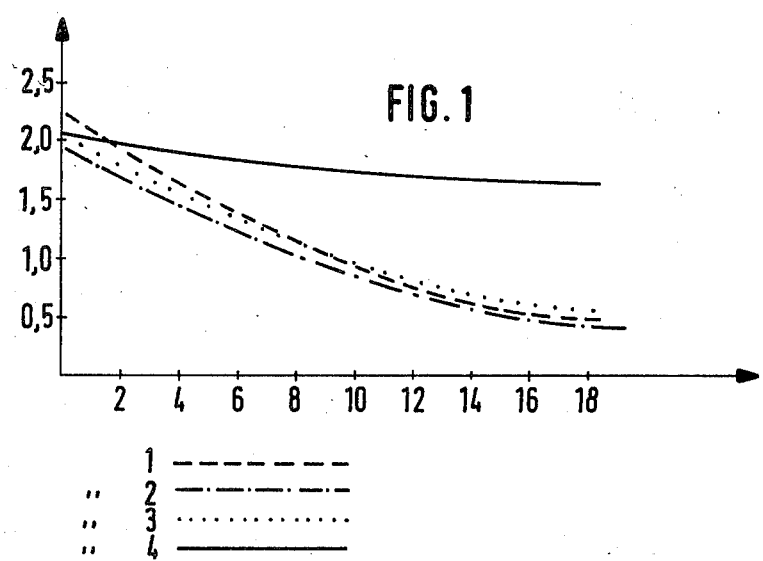
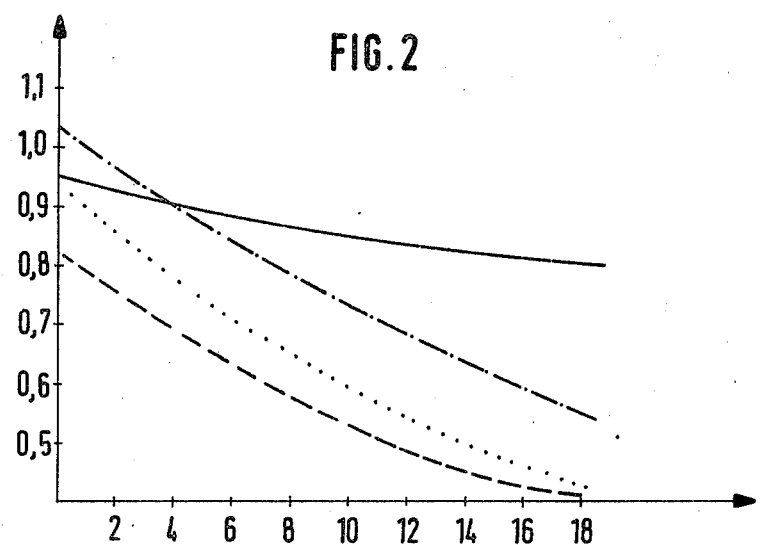

LIGHT-SENSITIVE DIAZOTYPE MATERIAL WITH 2-HYDROXY-3-NAPHTHOIC ACID AMIDES HAVING 6-SULFONIC ACID AMIDE SUBSTITUTION

This invention relates to 2-hydroxy-3-naphthoic acid amides which are substituted in the 6-position by a sulfonamide group.

Previously proposed 2-hydroxy-3-naphthoic acid amides which are not substituted in the 6-position (German Auslegeschrift No. 1,178,704) or are substituted by halogen or a lower alkoxy group (German Auslegeschrift No. 1,572,078) have been in use for some time as blue-copying couplers in diazotype materials. Combined with yellow or brown-coupling components, they also may be employed for black-copying diazotype materials.

Further, it is known from German Auslegeschrift No. 1,240,738, to use 1-hydroxy-naphthalene-8-sulfonamides as compounds capable of coupling in diazotype materials for the dry process, by which deep blue copies with a greenish tinge are obtained.

It is a disadvantage of these known couplers that their azo dyes which are formed upon coupling with the benzene diazonium compounds conventionally used in diazo printing, have only an inferior fastness to light which is, in some cases, even completely inadequate for the technical application. In fact, the well-known easy fading of azo dyes through the action of light leads to considerable problems in the technical application of diazo copies. The poor fastness to light of azo dyes is particularly unfavorable if a diazo copy, for example, an engineering drawing, is subjected to sunlight over a prolonged period of time, or if a so-called "diazo master" which is intended to be used for the production of further diazo copies is subjected to the actinic light of commercial diazo printers over a prolonged period of time.

The requirements concerning the fastness to light of the azo dyes are particularly high in the case of diazo microfilm copies which, in the continuous or repeated application of microfilms, serve as so-called "reading copies" or "working copies". Such diazo microfilm copies are used in readers or reader-printers to evaluate the information stored thereon, and they are thus subjected to a particularly strong impact by radiation (heat radiation, visible light, and UV radiation) from the sources of light of these apparatuses. It happens frequently that the dyestuff areas of diazo microfilm copies which are exposed for some time to the lamps employed in commercial readers, fade and lose contrast to such an extent that the information is only with difficulty discerned or is even entirely obliterated.

As is also known, urea and acrylamides (German Auslegeschrift No. 1,572,104) or so-called sterically hindered phenols carrying substituents in positions 2 and 4 (German Offenlegungsschrift No. 1,772,981) are added to the light-sensitive layer to stabilize the azo dyes contained therein and thus to prevent fading or the tendency towards yellowing of a diazo copy. It has become apparent, however, that in the practical application these two measures yield only improvements with respect to the degree of fading or yellowing.

It is, therefore, an object of the present invention to provide compounds which as blue-coupling components, together with the benzene diazonium compounds conventionally used in diazo printing, form azo dyes of an improved fastness to light, as compared with the known azo dyes.

This object is achieved by 2-hydroxy-3-naphthoic acid amides of the general formula:

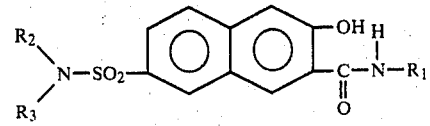

wherein:
$R_1$ is hydrogen, a substituted or unsubstituted alkyl, cycloalkyl, aralkyl, or aryl group, and
$R_2$ and $R_3$ are identical or different and are hydrogen, a substituted or unsubstituted alkyl, cycloalkyl aralkyl, or aryl group, or, together with the nitrogen atom to which they are attached, a substituted or unsubstituted heterocyclic group.

Favorable 2-hydroxy-3-naphthoic acid amides of the general formula are those in which $R_1$ represents hydrogen, an alkyl group containing up to 4 carbon atoms, a cycloalkyl group containing up to 12 carbon atoms, an aralkyl group containing up to 10 carbon atoms, or an aryl group containing up to 10 carbon atoms, which may be substituted by a hydroxy group, an alkyl group which may be substituted by halogen atoms, an alkoxy group, an acyl group, a halogen atom, or by amino groups which may be substituted by alkyl groups, or by a heterocyclic group; in which $R_2$ and $R_3$ are identical or different and represent hydrogen, an alkyl group containing up to 6 carbon atoms, a cycloalkyl group containing up to 6 carbon atoms, an aralkyl group containing up to 10 carbon atoms, or an aryl group containing up to 10 carbon atoms, which may be substituted by a hydroxy, a lower alkyl, an alkoxy, or an acyl group or by a halogen atom, or which, together with the nitrogen atom to which they are attached, represent a pyrrolidine, a piperidine, a piperazine, a thiomorpholine, or morpholine, or a hexamethyleneimine ring which may be substituted by an alkyl group. The preferred compounds are those in which $R_1$ and $R_2$ are an identical or a different aryl which may be substituted and $R_3$ represents hydrogen. Excellent results are obtained if compounds of the general formula are used, in which $R_1$ and $R_2$ are phenyl groups which may be substituted by at least one hydroxy, lower alkyl or alkoxy group, or by a halogen atom, and $R_3$ is hydrogen. The last-mentioned compounds are employed in diazo printing, especially in those cases in which sensitizing compositions based on organic solvents are used.

The 2-hydroxy-3-naphthoic acid amides of the invention provide coupling components for diazo printing, enabling the production of diazotype copies, particularly diazo microfilm copies, which meet the exacting demands with respect to fastness to light, and which retain color and contrast, even at an increased radiation load.

If aqueous sensitizing compositions are used, those compounds of the general formula are preferred, in which $R_1$ and/or $R_2$ are substituted by groups which render the compounds water-soluble, for example, hydroxy groups or alkoxy groups. Particularly preferred are compounds of the general formula, in which $R_1$ and/or $R_2$ are substituted by at least one basic group which may be present as such, as a salt, as a complex salt of a heavy metal, or as a quaternary ammonium salt.

Salt formation at the basic group may be effected in known manner using any acid capable of forming stable amine salts. For this purpose, the hydrochlorides are preferred. As the complex amine salts of heavy metals the complex salts of zinc chloride are preferred. If the basic group is quaternized, the fourth organic group is preferably a lower alkyl group. The basic group also may be a heterocyclic group. Preferred are basic heterocycles having from 5 to 8 ring members, for example, pyrrolidine, piperidine, piperazine, thiomorpholine, and hexamethyleneimine, particularly, however, morpholine.

Examples of 2-hydroxy-3-naphthoic acid amides according to the invention, which are preferably used as coupling components in diazotype materials are compiled in the list of formulae below, together with their melting or decomposition points, respectively.

The 2-hydroxy-3-naphthoic acid amides of the invention are prepared according to the following methods:

Method A

The 2-hydroxy-3-naphthoic acid amide-6-sulfonic acid amides which are substituted by alkyl or aralkyl groups $R_1$ are obtained as follows:

The potassium salt of 2-hydroxy-3-naphthoic acid-6-sulfonic acid is esterified in known manner in methanol/concentrated sulfuric acid, to form the potassium salt of 2-hydroxy-3-naphthoic acid-methyl ester-6-sulfonic acid. According to Schotten-Baumann, the phenolic hydroxy group is subsequently protected by reaction with benzene sulfonic acid chloride in an aqueous soda solution; and the sulfonic acid group is then converted into the sulfonic acid chloride group by reacting it with phosphorus oxychloride. The 2-benzene sulfonyloxy-3-naphthoic acid methyl ester-6-sulfonic acid chloride obtained melts at a temperature of about 156° to 157° C., and may be converted by conventional methods with the amine bases submitted by the groups $R_2$ and $R_3$, into the corresponding sulfonic acid amides. The 2-hydroxy-3-naphthoic acid amide-6-sulfonic acid amides according to the invention are obtained from the 2-benzene sulfonyloxy-3-naphthoic acid methyl ester-6-sulfonic acid amides by reacting the methyl esters with ammonia or primary aliphatic amines, according to the procedure described in Dutch Pat. No. 6,514,065, for the preparation of compound No. 12. In this reaction, the benzene sulfonyl protective group is simultaneously split-off. The compounds synthesized by this method are denoted by "A" in the list of formulae below.

Method B

To prepare the 2-hydroxy-3-naphthoic acid amide-6-sulfonic acid amides which are substituted by aryl or cycloalkyl groups $R_1$, the 2-benzene sulfonyloxy-3-naphthoic acid methyl ester-6-sulfonic acid amides prepared according to method A are briefly heated in an aqueous alkaline solution, whereby the carboxylic acid methyl esters are saponified and, at the same time, the benzene sulfonyl protective group is split-off. Then, known methods are employed to prepare the carboxylic acid chloride from the 2-hydroxy-3-naphthoic acid-6-sulfonic acid amides using thionyl chloride in an inert solvent, as described in German Auslegeschrift No. 1,572,078, Example 1, for the preparation of the carboxylic acid chlorides; and the carboxylic acid chloride is then, without isolating it, reacted with the primary amines substituted by the aryl or cycloalkyl groups $R_1$ to form the corresponding carboxylic acid amides.

The compounds synthesized by this method are denoted by "B" in the list of formulae below.

Any conventional substrate is suitable as a support material for diazotype layers, for example, coated or uncoated opaque or transparent papers, textiles, or plastic films. Particularly suitable plastic films are comprised of a cellulose ester, for example, cellulose 2½-acetate or tri-acetate, of a polyester, for example, polyethylene terephthalate, of vinyl polymers, for example, polyvinyl acetate or polyvinyl styrene.

The diazonium compounds which are used with the coupling components according to the present invention to produce blue color shades are already known. They are predominantly derivatives of the unilaterally diazotized p-phenylene diamine having at least one substituent in the amino group, for example, an alkyl or a hydroxyalkyl group. Of the diazonium compounds belonging to the unilaterally diazotized p-phenylene diamine type those are preferred which are substituted by an alkoxy group in position 2 and 5, and in which the substituents are linked to form a heterocyclic ring system, for example a morpholine ring system, at the amino nitrogen atom to which they are attached.

Together with the diazonium compounds, the 2-hydroxy-3-naphthoic acid amides of the invention form rich neutral blue to greenish-blue azo dyes. They have a greatly improved fastness to light, as compared with the conventional blue azo dyes.

In addition, the very faint inherent coloration of these new compounds constitutes an advantage over the known 2-hydroxy-3-naphthoic acid amides which are substituted in the 6-position, for example, by the methoxy group or by a bromine atom. The image backgrounds of diazocopies containing the inventive compounds as coupling components in their copying layers are, therefore, better than the backgrounds of diazocopies produced with the conventional coupling components.

A further advantage of the present 2-hydroxy-3-naphthoic acid amides over the known 2-hydroxy-3-naphthoic acid amides is their slower coupling speed. When these new coupling components are used in combination with the diazonium compounds of the p-phenylene diamine type which are preferred for two-component materials, this slower coupling speed results in a clearly improved stability of the unexposed diazotype material so produced, both under normal and also under moist climatic conditions. On account of the reduced coupling speed of these new coupling components, faster coupling diazonium compounds (for example, diazonium compounds which, in the p-position to the diazonium group, are substituted by a mercapto, phenyl, or acylamino group), which are normally used only in one-component diazotype materials, also may be employed for the preparation of two-component diazotype materials, without thereby affecting the storability of the material for practical applications.

As coupling components, the 2-hydroxy-3-naphthoic acid amides of the invention also may be mixed with one another, or they may be mixed with coupling components of other color shades, if it is desired to produce different color shades.

The coupling components of the invention, which are preferably used for two-component diazotype materials are, together with the diazonium compounds, applied to a suitable support, in known manner, from an aqueous, aqueous-alcoholic, or purely organic solution.

If plastic films serve as support materials, it has proved advantageous to apply the diazotype components to the layer support from a solution in an organic solvent medium which additionally contains a film-forming binder. The concentration of the dyestuff-forming components in the binder may vary between 15 and 30 parts by weight of the dyestuff-forming components per 100 parts by weight of the binder.

Suitable binders are, for example, a variety of polymer substances, e.g., cellulose ethers, such as ethyl cellulose, or cellulose esters, such as cellulose acetate, cellulose triacetate, cellulose acetopropionate, cellulose butyrate, and cellulose acetobutyrate, or vinyl polymers, such as polyvinyl acetate, polyvinylidene chloride, copolymers of vinyl chloride and vinyl acetate, poly-(methylmethacrylate) copolymers of alkyl acrylates and acrylic acid, or further polymers, for example, polyphenylene oxide and terpolymers of ethylene glycol/isophthalic acid/terephthalic acid.

Apart from the dyestuff-forming components, the light-sensitive layer additionally may contain acid stabilizers, for example, hydrochloric acid, boric acid, citric acid, tartaric acid, formic acid, and 5-sulfosalicylic acid and other conventional auxiliary substances for diazo printing.

Frequently, the sensitizing solutions contain inorganic salts, for example, zinc chloride and ammonium sulfate to increase contrast; and additions which act as solubilizers and coupling accelerators, for example, urea or thiourea; or organic solvents, for example, acetone, methyl ethyl ketone, ethylene glycol, ethylene glycol monomethyl ether, glycerol, glycerol di-acetate, and glycerol triacetate, etc.

Further, agents which prevent yellowing and plasticizers may be added to the light-sensitive layer. It is also possible to incorporate weakly concentrated dyestuffs in the diazotype layer to stain the fully exposed areas of the copy.

The invention will be further illustrated by reference to the following specific examples:

Explanations Concerning the Examples

A. The base lacquer used for the preparation of the diazotype materials in Examples 1 to 5 contains 7.5 percent by weight of cellulose acetopropionate, dissolved in a solvent mixture composed of acetone, methanol, n-butanol, and glycol monomethyl ether.

B. The optical densities of the full-shade samples in Examples 1 to 5 are measured by means of a "MACBETH Quantalog-Densitometer".

For density measurement in the visual spectral range a filter acting in the range between 510 and 580 nm is used, and for density measurement in the ultraviolet spectral range a filter acting in the range between 310 and 410 nm is used.

C. The following apparatuses are employed to test and evaluate the fastness to light of the diazotype dyes in the full-shade samples of Examples 1 to 5:

An ordinary reader equipped with an incandescent lamp of 15 V/150 watts and a lens capable of 24 times magnification at maximum brightness setting.

A fluorescent tube tester including 5 fluorescent tubes, Philips TLAD 15 W/05. The spectral composition of the radiation emitted by the fluorescent tubes corresponds approximately to the spectral composition of sunlight.

D. The full-shade samples of Examples 1 to 5 are developed in the conventional manner using damp ammonia vapor in the developing section of a commercial duplicator for microfilm sheets.

The imagewise exposure of the diazotype materials of Example 6 and subsequent developing of the latent diazotype copies are carried out in a commercial diazo printer.

EXAMPLE 1

100 ml each of base lacquer are used to prepare four different coating solutions having the following compositions:
  360 mg of sulfosalicylic acid,
  420 mg of 2,5-dibutoxy-4-morpholino-benzene-diazonium fluoborate,
  $1 \times 10^{-3}$ mole of a blue coupler,
with the following compositions being used as the blue couplers:
1. 2-hydroxy-3-naphthoic acid-N(2'-methyl-phenyl)-amide,
2. 6-methoxy-2-hydroxy-3-naphthoic acid-N(2'-methyl-phenyl)-amide,
3. 6-bromo-2-hydroxy-3-naphthoic acid-N(2'-methyl-phenyl)-amide,
4. 2-hydroxy-3-naphthoic acid-N(2'-methyl-phenyl)-amide-6-sulfonic acid-N(phenyl)-amide (No. 16 in the list of formulae below)

Each solution is applied to a polyethylene terephthalate film provided with an adhesive layer and having a thickness of 100 μm so that after drying in a return-air drying cabinet at 60° to 70° C. the different diazotype materials obtained can be developed to a visual optical density of about 2.

According to the sensitizing solutions employed, the diazotype materials prepared are consecutively numbered from 1 to 4.

Diazotype material 1 develops to a reddish-blue azo dye, whereas diazotype materials 2 to 4 develop to greenish-blue azo dyes.

In order to ensure that coupling into the azo dyes has been completed in the light-sensitive layers, each of the four different diazotype materials is developed twice.

Then, the diazotype materials which have been developed to full shade are exposed to diffuse daylight over a period of 12 hours.

A strip of 0.5 cm × 5 cm is cut from each of the full-shade samples treated in this manner, and this strip is marked by a circular measuring area of about 0.3 cm². In each measuring area the optical density (D) is determined in the green and ultraviolet spectral ranges. Then the marked strips are simultaneously exposed to the spectral emission from the source of light of a reader. Following irradiation periods of two hours each, the optical densities ($D_{END}$) of the full-shade samples are again determined and compared with the initial densities ($D_{BEG}$). Irradiation of the full-shade samples in the reader is continued until the visual optical density of one sample has dropped to $\leq 0.5$.

To evaluate the fastness to light of the azo dyes in full-shade samples 1 to 4, their optical densities at the beginning (BEG) of the irradiation test and after an irradiation time of 18 hours (END) in the reader are compiled in Table 1 below.

TABLE 1

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 1 | 2.29 | 0.44 | 19 | 0.83 | 0.36 | 43 |

TABLE 1-continued

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 2 | 2.01 | 0.42 | 21 | 1.04 | 0.54 | 52 |
| 3 | 2.12 | 0.48 | 23 | 0.95 | 0.42 | 44 |
| 4 | 2.11 | 1.64 | 78 | 0.95 | 0.80 | 84 |

A comparison of the optical density values shows very impressively the outstanding fastness to light of full-shade sample 4 in the visual and also in the ultraviolet spectral range.

After 18 hours in the reader, the azo dye of full-shade sample 4 has still 78% of its original visual density, whereas the azo dyes of comparative samples 1 to 3 have already dropped to about 20% of their original visual densities.

FIGS. 1 and 2 show, in the form of graphs, the measured optical densities of full-shade samples 1 to 4 as functions of the irradiation time in the reader, in the ranges between 510 and 580 nm (FIG. 1) and between 310 and 410 nm (FIG. 2).

After 18 hours in the reader the color shade of full-shade sample 4 has not changed, while the color shades of full-shade samples 1 to 3 have been shifted from initially blue to red.

A second strip of 3 cm×5 cm is cut from each of samples 1 to 4 which have been developed to full shade and stored for 12 hours in diffuse daylight, and each of these strips is marked by a circular measuring area of about 0.3 cm². The optical densities ($D_{BEG}$) in the green and ultraviolet spectral ranges are determined in these measuring areas, and the samples are then placed in a closed metal container and exposed for 96 hours to the spectral emission of 5 fluorescent tubes. Then, the optical densities ($D_{END}$) are again determined in the measuring areas.

Table 2 gives the results of these measurements.

TABLE 2

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 1 | 2.20 | 1.76 | 80 | 0.81 | 0.72 | 89 |
| 2 | 1.75 | 1.50 | 86 | 0.91 | 0.85 | 93 |
| 3 | 1.93 | 1.69 | 87 | 0.88 | 0.81 | 91 |
| 4 | 2.07 | 1.95 | 94 | 0.95 | 0.90 | 95 |

A comparison of the density values shows that the azo dye of full-shade sample 4 has undergone the least change of optical density by the spectral emission of the fluorescent tubes.

EXAMPLE 2

100 ml each of base lacquer are used to prepare 5 different coating solutions having the following compositions:
 360 mg of sulfosalicylic acid,
 420 mg of 2,5-dibutoxy-4-morpholino benzene diazonium fluoborate,
 $1 \times 10^{-3}$ mole of a blue coupler,
with the following compositions being used as the blue couplers:
5. 2-hydroxy-3-naphthoic acid-N(3'-morpholino-propyl)-amide,
6. 6-methoxy-2-hydroxy-3-naphthoic acid-N(3'-morpholino-propyl)-amide,
7. 6-bromo-2-hydroxy-3-naphthoic acid-N(3'-morpholino-propyl)-amide,
8. 8-hydroxy-5-methyl-naphthalene sulfonic acid amide(1),
9. 2-hydroxy-3-naphthoic acid-N(3'-morpholino-propyl)-amide-6-sulfonic acid-N(phenyl)-amide (No. 3 in the list of formulae below).

As described in Example 1, consecutively numbered diazotype materials are prepared from each solution. Each sample is developed to full shade, as in Example 1, and the full-shade samples thus obtained are tested for fastness to light.

Diazotype material 5 develops to a reddish-blue color shade, whereas diazotype materials 6 to 9 develop to greenish-blue color shades.

To evaluate the fastness to light of the azo dyes of full-shade samples 5 to 9, their optical densities (D) at the beginning (BEG) of the irradiation test and after 10 hours (END) (except for sample 8) irradiation time in the reader are given in the following table.

TABLE 3

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 5 | 2.20 | 0.45 | 20 | 0.73 | 0.32 | 44 |
| 6 | 1.87 | 0.28 | 15 | 0.87 | 0.39 | 45 |
| 7 | 2.26 | 0.24 | 11 | 0.87 | 0.27 | 31 |
| 8 | 1.92 | 0.63 | 33 | 0.80 | 0.44 | 55 |
| 9 | 2.07 | 1.38 | 67 | 0.82 | 0.64 | 78 |

The density values measured show that in the reader the azo dye of full-shade sample 9 is by far more stable to light than the azo dyes of full-shade samples 5 to 8. Following 10 hours irradiation in the reader the azo dye of full-shade sample 9 still has 67% of its original visual density, whereas the azo dyes of comparative samples 5 to 8 are almost entirely destroyed, while sample 8 has become useless after 6 hours irradiation.

The color shade of full-shade sample 9 is unchanged after 10 hours irradiation in the reader, while the color shades of samples 5 to 8 have been shifted from initially blue to red.

The fastness to light of the azo dyes in the fluorescent tube tester is tested as described in Example 1.

The changing optical densities ($D_{BEG \rightarrow END}$) over an irradiation time of 96 hours are given in the table below.

TABLE 4

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 5 | 2.21 | 1.01 | 45 | 0.73 | 0.47 | 64 |
| 6 | 1.85 | 0.89 | 48 | 0.86 | 0.59 | 69 |
| 7 | 2.28 | 1.55 | 68 | 0.87 | 0.70 | 81 |
| 8 | 1.85 | 0.96 | 52 | 0.77 | 0.57 | 74 |
| 9 | 1.90 | 1.56 | 82 | 0.76 | 0.67 | 88 |

The density values show that the azo dye of full-shade sample 9 has undergone the least destruction by the emission of the fluorescent tubes.

EXAMPLE 3

100 ml each of base lacquer are used to prepare four different coating solutions:
 360 mg of sulfosalicylic acid,
 420 mg of 2,5-dibutoxy-4-morpholino benzene diazonium fluoborate, and $1 \times 10^{-3}$ mole of a blue coupler.

The following blue couplers are employed:

10. 2-hydroxy-3-naphthoic acid-N(phenyl)-amide-6-sulfonic acid amide, (No. 10 in the list of formulae below)
11. 2-hydroxy-3-naphthoic acid-N(phenyl)-amide-6-sulfonic acid-N(2'-methoxy ethyl)-amide, (No. 12)
12. 2-hydroxy-3-naphthoic acid-N(phenyl)-amide-6-sulonic acid morpholide, (No. 25)
13. 2-hydroxy-3-naphthoic acid-N(phenyl)-amide-6-sulfone-N(methyl-phenyl)-amide, (No. 24).

As described in Example 1, a diazotype material is prepared from each solution and consecutively numbered from 10 to 13 according to the solution used; the samples are then developed. Following airing and fully exposing the full-shade samples thus obtained the fastness to light of their azo dyes is evaluated as in Examples 1 and 2.

Diazotype materials 10 to 13 develop to greenish-blue color shades.

To evaluate the fastness to light of full-shade samples 10 to 13, their optical densities (D) at the beginning (BEG) of the irradiation test and after 18 hours irradiation (END) in the reader are compiled in the following table:

TABLE 5

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 10 | 1.69 | 1.06 | 63 | 0.85 | 0.63 | 74 |
| 11 | 2.45 | 1.64 | 67 | 1.04 | 0.81 | 78 |
| 12 | 2.38 | 1.67 | 73 | 1.01 | 0.82 | 81 |
| 13 | 1.94 | 1.40 | 72 | 0.92 | 0.74 | 81 |

The density values measured show that the loss of density of full-shade samples 10 to 13 in the visual and ultra-violet spectral ranges is approximately equal after 18 hours in the reader. The stability to light of the azo dyes of full-shade samples 12 and 13 is slightly better than that of the azo dyes of samples 10 and 11.

If these density values are compared with the values of Table 1, obtained with full-shade samples 1 to 3 after 18 hours irradiation in the reader, the outstanding stability to light of the azo dyes of full-shade samples 10 to 13 becomes apparent.

After 18 hours in the reader, the color shade of full-shade sample 10 has been shifted from an initially greenish-blue to a reddish-blue color shade.

To evaluate the fastness to light of the azo dyes in the fluorescent tube tester the method described in Examples 1 and 2 is used.

The changing optical densities (D) of the azo dyes during an irradiation time of 96 hours are listed in Table 6.

TABLE 6

| Sample | Visual Density | | | UV Density | | |
|---|---|---|---|---|---|---|
| | $D_{BEG}$ | $D_{END}$ | Residual Density % | $D_{BEG}$ | $D_{END}$ | Residual Density % |
| 10 | 1.52 | 1.28 | 84 | 0.78 | 0.71 | 91 |
| 11 | 2.25 | 2.11 | 94 | 0.98 | 0.93 | 95 |
| 12 | 2.02 | 1.88 | 93 | 0.93 | 0.91 | 95 |
| 13 | 1.77 | 1.62 | 92 | 0.85 | 0.81 | 95 |

The density values show that the fastness to light of the azo dye of full-shade sample 10 is slightly inferior to that of the azo dyes of full-shade samples 11 to 13.

On the other hand, a comparison with the density values of full-shade samples 4 and 9 in Examples 1 and 2 shows that the drop of density during an irradiation time of 96 hours in the fluorescent tube tester is practically equal.

It further can be seen from the results of the measurements that a secondary or tertiary sulfonic acid amide group in the 6-position of the 2-hydroxy-3-naphthoic acid amide molecule has a more beneficial influence on the fastness to light of the azo dyes obtainable with these compounds, than a primary sulfonic acid amide group in the same position.

EXAMPLE 4

100 ml each of base lacquer are used to prepare five different coating solutions having the following compositions:

744 mg of sulfosalicylic acid,
153 mg of zinc chloride,
600 ml of glycerol triacetate,
168 mg of thiourea,
153 mg of 2-methyl-resorcinol,
30 mg of 2,2', 4,4'-tetrahydroxy-diphenyl sulfide,
660 mg of 2,5-dibutoxy-4-morpholino-benzene diazonium fluoborate,
70 mg of 4-(dipropylamino)-benzene diazonium fluoborate, and
$2 \times 10^{-3}$ mole of a blue coupler, with the following compositions being used as the blue couplers:

14. 2-hydroxy-3-naphthoic acid-N(2'-methyl-phenyl)-amide-6-sulfonic acid-N(phenyl)-amide, (No. 16)
15. 2-hydroxy-3-naphthoic acid-N(phenyl)-amide-6-sulfonic acid-N(phenyl)-amide, (No. 15)
16. 6-methoxy-2-hydroxy-3-naphthoic acid-N(3'-morpholino-propyl)-amide,
17. 2-hydroxy-3-naphthoic acid-N(3'-morpholino-propyl)-amide,
18. 2-hydroxy-3-naphthoic acid-N(2'-methyl-phenyl)-amide.

As described in Example 1, each of the solutions is applied to a polyethylene terephthalate film provided with an adhesive layer and having a thickness of 100 μm; the back of the film carries a coating pigmented with silicon dioxide and aluminum oxide. The sensitizing solution is applied in such a manner that, following drying, the different diazotype materials can be developed to a visual optical density (D) ranging between 1.5 and 2.5.

The developed full-shade samples are consecutively numbered from 14 to 18 according to the coating solution used.

Diazotype materials 14 and 15 develop to a neutral black color shade, diazotype material 16 to a dark blue color shade with a greenish tinge, diazotype material 17 to a violet color shade, and diazotype material 18 to a reddish-blue color shade.

As in Example 1, a test strip is cut from each full-shade sample and is exposed to the spectral emission from the source of light of the reader.

The following table gives the optical densities of the azo dyes of full-shade samples 14 to 18, determined at the beginning (BEG) of the irradiation test and after 10 hours (END) in the reader, to evaluate their fastness to light.

TABLE 7

| Sam- | Visual Density | | | UV Density | | |
|---|---|---|---|---|---|---|
| ple | $D_{BEG}$ | $D_{END}$ | Residual Density % | $D_{BEG}$ | $D_{END}$ | Residual Denstiy % |
| 14 | 1.66 | 1.35 | 82 | 1.25 | 1.15 | 92 |
| 15 | 1.74 | 1.45 | 83 | 1.34 | 1.23 | 92 |
| 16 | 2.14 | 1.24 | 58 | 1.43 | 1.27 | 89 |
| 17 | 2.34 | 1.22 | 52 | 1.16 | 0.97 | 83 |
| 18 | 2.55 | 1.44 | 56 | 1.21 | 1.02 | 85 |

A comparison of the optical densities measured shows that after 10 hours in the reader the azo dyes of full-shade samples 14 and 15 are, particularly in the visual spectral range, by far more stable to light than the azo dyes of full-shade samples 16 to 18.

Similar results with respect to the fastness to light are obtained if a natural transparent paper, as conventionally used in diazo printing, is employed instead of the polyethylene terephthalate film which is pigmented on one side.

EXAMPLE 5

A polyethylene terephthalate film provided with an adhesive layer is coated on the primed surface with a solution having the following composition:
  100 ml of base lacquer,
  360 mg of sulfosalicylic acid,
  10 mg of thiourea,
  420 mg of 2-hydroxy-3-naphthoic acid-N(pheny)-amide-6-sulfonic acid-N(phenyl)-amide, (No. 15), and
  410 mg of 6-chloro-4-dimethyl amino-3(4-chlorophenoxy)-benzene diazonium chloride (zinc chloride double salt).

After drying the sensitized film, development is carried out in damp ammonia vapor, as usual. Upon a single passage through the developing section of a commercial duplicator, the diazotype material develops to a strong reddish-blue color shade, the visual density (D) of which does not change, even upon repeated developing. The unexposed diazotype material is sufficiently stable under tropical climatic conditions.

EXAMPLE 6

A conventional diazo base paper precoated on one side with colloidal silicic acid and polyvinyl acetate is coated on the primed surface with a solution having the following composition:
  100 ml of water,
  4 g of citric acid,
  5 g of thiourea,
  2.3 g of 2-hydroxy-3-naphthoic acid-N(3'-morpholino-propyl)-amide-6-sulfonic acid-N (phenyl)-amide (zinc chloride complex salt), (No. 4), and
  1.5 g of 2,5-diethoxy-4-morpholino-benzene diazonium chloride (zinc chloride double salt).

After drying, the sensitized paper is imagewise exposed under a transparent original, and the latent copy is then developed with damp ammonia vapor in a commercial diazo printer. A greenish-blue image on a white background is obtained.

The unexposed diazotype material has a very good stability under tropical climatic conditions, and the fastness to light of the greenish-blue azo dye images of the diazotype copies, as determined in the fluorescent tube tester, is excellent.

If the coupler of the invention is replaced by a conventional blue coupler, for example, 1.4 g of 2-hydroxy-3-naphthoic acid-N(3'-morpholino-propyl)-amide (hydrochloride), a reddish-blue image on a faintly beige background is obtained after imagewise exposure and subsequent development. The corresponding unexposed diazotype material is less stable, and the fastness to light of the azo dye image is poorer than with the blue coupler of the invention.

EXAMPLE 7

White diazo base paper precoated on one side with colloidal silicic acid and polyvinyl acetate, is coated on the primed surface with a solution having the following composition:
  100 ml of water,
  0.5 g of tartaric acid,
  0.1 g of saponin,
  1.6 g of the zinc chloride double salt of 2,5-diethoxy-4(4'-methyl-phenyl-mercapto)-benzene diazonium chloride.

After drying, the sensitized paper is imagewise exposed under a transparent original, and the latent copy is then developed using a solution of the following composition:
  100 ml of water,
  1.0 g of potassium hydroxide,
  0.1 g of the sodium salt of an alkyl naphthalene sulfonic acid,
  1.5 g of 2-hydroxy-3-naphthoic acid-N(phenyl)amide-6-sulfonic acid-N(3'-methoxypropyl)-amide (No. 13).

The copy of the original has neutral blue lines, and the azo dye image exhibits a very good fastness to light when tested in the fluorescent tube tester.

| No. | $R_1$ | $R_2$ | $R_3$ | Melting Point (°C.) | Preparation Method |
|---|---|---|---|---|---|
| 1 | H | —⟨phenyl⟩ | H | 233–235 | A |
| 2 | —(CH$_2$)$_2$—OH | —⟨phenyl⟩ | H | 187–188 | A |
| 3 | —(CH$_2$)$_3$—N(morpholino) | —⟨phenyl⟩ | H | 163–165 | A |
| 4 | —(CH$_2$)$_3$—N(morpholino) · ZnCl$_2$ HCl | —⟨phenyl⟩ | H | 124 (Decomp.) | A |

-continued

| No. | R₁ | R₂ | R₃ | Melting Point (°C.) | Preparation Method |
|---|---|---|---|---|---|
| 5 | —(CH₂)₂—N(morpholino)·HPF₆ | phenyl | H | 100 (Decomp.) | A |
| 6 | —(CH₂)₂—N(C₂H₅)₂ | phenyl | H | 107–110 | A |
| 7 | —(CH₂)₂—phenyl | phenyl | H | 207–209 | A |
| 8 | H (cyclohexyl) | phenyl | H | 223–225 | B |
| 9 | (CH₂)₃—N(morpholino)·HCl | —C₂H₅ | —C₂H₅ | 214–216 | A |
| 10 | phenyl | H | H | 274 (decomp.) | B |
| 11 | phenyl | —C₄H₉(n) | H | 208–209 | B |
| 12 | phenyl | —(CH₂)₂—OCH₃ | H | 210–213 | B |
| 13 | phenyl | —(CH₂)₃—OCH₃ | H | 176–177 | B |
| 14 | phenyl | —CH₂—phenyl | H | 234–236 | B |
| 15 | phenyl | phenyl | H | 241–243 | B |
| 16 | CH₃-phenyl | phenyl | H | 232–233 | B |
| 17 | CH₃-phenyl | CH₃-phenyl | H | 228–229 | B |
| 18 | CH₃-phenyl-Cl | CH₃-phenyl-Cl | H | 250–251 | B |
| 19 | CH₃O-phenyl(OCH₃)(OCH₃) | phenyl | H | 252–253 | B |
| 20 | HO-phenyl | HO-phenyl | H | 253–254 | B |
| 21 | phenyl-N(C₂H₅)₂ | —(CH₂)₂—OCH₃ | H | 207–208 | B |
| 22 | phenyl-N(C₂H₅)₂·HCl | —(CH₂)₂—OCH₃ | H | 241–243 (decomp.) | B |
| 23 | CH₃-phenyl | —C₂H₅ | —C₂H₅ | 242–243 | B |
| 24 | phenyl | —CH₃ | phenyl | 221–223 | B |
| 25 | phenyl | morpholino (O/N/H) | | 244–245 | B |
| 26 | phenyl-CF₃ | phenyl | H | 257–259 | B |
| 27 | CH₃O-phenyl | phenyl | H | 225–227 | B |

-continued

| No. | R₁ | R₂ | R₃ | Melting Point (°C.) | Preparation Method |
|---|---|---|---|---|---|
| 28 | 4-acetylphenyl | phenyl | H | 264–265 | B |
| 29 | 3,4-dimethoxyphenyl | phenyl | H | 214–215 | B |
| 30 | 4-methoxyphenyl | —(CH₂)₃—OCH₃ | H | 156–157 | B |
| 31 | 3,4-dimethoxyphenyl | —(CH₂)₃—OCH₃ | H | 151–153 | B |
| 32 | 2,5-diethoxy-4-chlorophenyl | —(CH₂)₃—OCH₃ | H | 162–163 | B |
| 33 | phenyl | —CH₃ | H | 244–245 | B |
| 34 | —CH₃ | —CH₃ | H | 248–249 | A |
| 35 | 2,5-diethoxy-4-chlorophenyl | phenyl | H | 237–239 | B |
| 36 | 4-methoxyphenyl | phenyl | H | 249–250 | B |
| 37 | 2,3-dimethylphenyl | phenyl | H | 233–236 | B |
| 38 | 4-methylphenyl | 4-methylphenyl | H | 263–264 | B |
| 39 | 2,4-dimethylphenyl | 2,4-dimethylphenyl | H | 219–222 | B |
| 40 | 3,4-dimethylphenyl | 3,4-dimethylphenyl | H | 220–223 | B |
| 41 | 2,3-dimethylphenyl | 4-methylphenyl | H | 211–213 | B |
| 42 | 2,3-dimethylphenyl | 2,3-dimethylphenyl | H | 268–273 | B |

It will be obvious to those skilled in the art that many modifications may be made within the scope of the present invention without departing from the spirit thereof, and the invention includes all such modifications.

What is claimed is:

1. In a diazotype material comprising a light-sensitive layer on a support, said layer containing at least one photosensitive diazonium compound from the group consisting of (1) unilaterally diazotized p-phenylene diamine with alkoxy group in positions 2 and 5 relative the diazonium radical; (2) p-mercapto benzene diazonium compound; (3) p-phenyl benzene diazonium compound; (4) p-acylamino benzene diazonium compound; and (5) 6-chloro-4-dimethylamino-3(4-chlorophenoxy)-benzene diazonium compound at least one coupling component, a binder, and an acid stabilizer, the improvement that the coupling component is at least one 2-hydroxy-3-naphthoic acid amide of the general formula

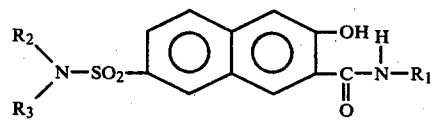

wherein
R₁ is hydrogen, a substituted or unsubstituted alkyl, cycloalkyl, aralkyl or aryl group, and
R₂ and R₃ are identical or different and are hydrogen, a substituted or unsubstituted alkyl, cycloalkyl, aralkyl or aryl group, or together with the nitrogen atom to which they are attached, a substituted or unsubstituted heterocyclic group.

2. A diazotype material according to claim 1 wherein $R_1$ and $R_2$ are identical or different, substituted or unsubstituted aryl groups and $R_3$ is hydrogen.

3. A diazotype material according to claim 1 wherein $R_1$ is hydrogen, an alkyl group containing up to 4 carbon atoms, a cycloalkyl group containing up to 12 carbon atoms, an aralkyl group containing up to 10 carbon atoms, or an aryl group containing up to 10 carbon atoms, which may be substituted by a hydroxy group, an alkyl group which may be substituted by halogen atoms, an alkoxy group, an acyl group, a halogen atom, by amino groups which may be substituted by alkyl groups, or by a heterocyclic group; in which $R_2$ and $R_3$ are identical or different and represent hydrogen, an alkyl group containing up to 6 carbon atoms, a cycloalkyl group containing up to 6 carbon atoms, an aralkyl group containing up to 10 carbon atoms, or an aryl group containing up to 10 carbon atoms, which may be substituted by a hydroxy, a lower alkyl, an alkoxy, or an acyl group, or by a halogen atom or which, together with the nitrogen atom to which they are attached, represent a pyrrolidine, a piperidine, a piperazine, a thiomorpholine, a morpholine, or a hexamethyleneimine ring which may be substituted by an alkyl group.

4. A diazotype material according to claim 1 wherein $R_1$ and $R_2$ are phenyl groups which may be substituted by at least one hydroxy, lower alkyl or alkoxy group or by a halogen atom, and wherein $R_3$ is hydrogen.

5. A diazotype material according to claim 1 wherein at least one of $R_1$ and $R_2$ is substituted by at least one basic group.

6. A diazotype material according to claim 1 in which the coupling component is 2-hydroxy-3-naphthoic acid-N(3'-morpholino-propyl)-amide-6-sulfonic acid-N(phenyl)-amide.

7. A diazotype material according to claim 1 in which the coupling component is 2-hydroxy-3-naphthoic acid-N(phenyl)-amide-6-sulfonic acid-N(3'-methoxypropyl)-amide.

8. A diazotype material according to claim 1 in which the coupling component is 2-hydroxy-3-naphthoic acid-N(phenyl)-amide-6-sulfonic acid-N(phenyl)-amide.

9. A diazotype material according to claim 1 in which the coupling component is 2-hydroxy-3-naphthoic acid-N(2'-methylphenyl)-amide-6-sulfonic acid-N(phenyl)-amide.

10. A diazotype material according to claim 1 in which the coupling component is 2-hydroxy-3-naphthoic acid-N(2'-methylphenyl)-amide-6-sulfonic acid-N(2'-methylphenyl)-amide.

* * * * *